United States Patent
Laaksonen et al.

(10) Patent No.: US 9,541,565 B2
(45) Date of Patent: Jan. 10, 2017

(54) BIOMARKERS FOR SENSITIVE DETECTION OF STATIN-INDUCED MUSCLE TOXICITY

(75) Inventors: Reijo Laaksonen, Lempäälä (FI); Kim Ekroos, Espoo (FI); Reini Hurme, Espoo (FI); Minna Jänis, Espoo (FI); Riikka Katainen, Helsinki (FI); Kirill Tarasov, Espoo (FI)

(73) Assignee: ZORA BIOSCIENCES OY, Espoo (FI)

( * ) Notice: Subject to any disclaimer, the term of this patent is extended or adjusted under 35 U.S.C. 154(b) by 0 days.

(21) Appl. No.: 13/332,773

(22) Filed: Dec. 21, 2011

(65) Prior Publication Data

US 2012/0258123 A1 Oct. 11, 2012

Related U.S. Application Data

(63) Continuation of application No. PCT/EP2011/055569, filed on Apr. 8, 2011.

(60) Provisional application No. 61/545,603, filed on Oct. 11, 2011.

(51) Int. Cl.
G01N 33/92 (2006.01)

(52) U.S. Cl.
CPC ........... *G01N 33/92* (2013.01); *G01N 2800/10* (2013.01); *G01N 2800/2871* (2013.01); *G01N 2800/325* (2013.01)

(58) Field of Classification Search
CPC ............................ G01N 33/92; G01N 2800/52
See application file for complete search history.

(56) References Cited

U.S. PATENT DOCUMENTS

| 7,611,902 | B2 | 11/2009 | Laaksonen et al. |
| 2004/0143461 | A1 | 7/2004 | Watkins |
| 2009/0029473 | A1 | 1/2009 | Han |
| 2009/0197242 | A1 | 8/2009 | Kaddurah-Daouk et al. |

FOREIGN PATENT DOCUMENTS

| CN | 1211184 A | 3/1999 |
| CN | 101189005 A | 5/2008 |
| CN | 101522910 | 9/2009 |
| JP | 2009-540314 A | 11/2009 |
| JP | 2010-500566 A | 1/2010 |
| WO | 97/29751 | 8/1997 |
| WO | 03079026 | 9/2003 |
| WO | 2004085610 | 10/2004 |
| WO | 2006/129859 A2 | 12/2006 |
| WO | 2007061995 | 5/2007 |
| WO | 2007/100782 | 9/2007 |
| WO | 2007127192 | 11/2007 |
| WO | 2007144467 | 12/2007 |
| WO | 2007144467 A1 | 12/2007 |
| WO | 2008021192 A1 | 2/2008 |
| WO | 2010/108737 A1 | 9/2010 |
| WO | 2011063470 | 6/2011 |
| WO | 2011/138419 | 11/2011 |
| WO | 2011/161062 | 12/2011 |
| WO | 2012/136272 | 10/2012 |

OTHER PUBLICATIONS

Laaksonen, Reijo et al. A Systems Biology Strategy Reveals Biological Pathways and Plasma Biomarker Candidates for Potentially Toxic Statin-Induced Changes in Muscle. PLoS One. Dec. 2006, 1:e97.
Laaksonen, Reijo et al. Lipidomics-Based Safety Biomarkers for Lipid-Lowering Treatments. Angiology. Apr. 2008, 59(2), suppl. 1:65S-68S.
Laaksonen. R. Predicting Statin Induced Muscle Toxicity. Journal of Clinical Lipidology. Jun. 2011, 5(3):239-240.
Kaddurah-Daouk, Rima et al. Lipidomic analysis of variation in response to simvastatin in the Cholestrol and Pharmacogenetics Study. Metabotomics. Jun. 1, 2010, 6(2):191-201.
Ekroos, Kim et al. Lipidomics: A Tool for Studies of Atherosclerosis. Current Atherosclerosis Reports. Jul. 2010, 12:273-281.
Waterman, Claire L. et al. Metabolomic strategies to study lipotoxicity in cardiovascular disease. Biochimica and Byophysica Acta. Mol. Cell Biology of Lipids. Mar. 1, 2010, 1801(3):230-234.
Hu, Chunxiu et al. Analytical strategies in lipidomics and applications in disease biomarker discovery. Journal of Chomatography. Sep. 15, 2009, 877(26):2836-2846.
Stahlman, Marcus et al. High-throughput shotgun lipidomics by quadrupole time-of-flight mass spectrometry. Journal of Chromatography. Sep. 15, 2009, 877(26):2664-2672.
Janis, Minna T. et al. Metabolomic strategies to identify tissue-specific effects of cardiovascular drugs. Expert Opinion on Drug Metabolism & Toxicology. Jun. 2008, 4(6):665-880.
Laaksonen, R. et al. Lipidomics as a tool for atherosclerosis research. New Biotechnology. Apr. 1, 2010, 27:S18-S19.
Nardin, Rachel A. et al., Effect of Newly Proposed CK Reference Limits on Neuromuscular Diagnosis, Muscle & Nerve, 39, Apr. 2009, pp. 494-497.
Eckel, Robert H., Approach to the Patient Who Is Intolerant of Statin Therapy, J. Clin. Endocrinol. Metab, May 2010, 95(5):2015-2022.

(Continued)

*Primary Examiner* — Ruixiang Li
(74) *Attorney, Agent, or Firm* — MH2 Technology Law Group, LLP

(57) ABSTRACT

The present invention inter alia provides a method, and uses thereof, of predicting statin-induced muscle toxicity or its complications, such as myalgia, myopathy and rhabdomyolysis, by detecting the lipid concentrations or lipid-lipid concentration ratios of a biological sample and comparing them to a control. This method has identified lipid markers that are more specific and sensitive in detecting these statin-induced muscle toxicity than the currently utilized clinical markers. Also provided is an antibody towards said lipids, and the use thereof for predicting, diagnosing, statin-induced muscle toxicity. The invention additionally relates to kits comprising lipids and/or an antibody thereto, for use in the prediction and/or diagnosis of statin-induced muscle toxicity.

20 Claims, No Drawings

(56) References Cited

OTHER PUBLICATIONS

Blaier, O. et al., Managing statin-induced muscle toxicity in a lipid clinic, Journal of Clinical Pharmacy and Terapeutics, 2011, 36:336-341.
Kenney, Kimbra et al., Serum Creatine Kinase After Exercise: Drawing the Line Between Physiological Response and Exertional Rhabdomyolysis, Muscle & Nerve, Mar. 2012, pp. 356-362.
Mayo Clinic CK Test, Test Definition: CK, Creatine Kinase (CK), Serum, Sep. 19, 2012, 1 Page.
Quest Diagnostics CK Test, Oct. 26, 2012, 2 Pages.
Sterz, Katherina et al., A simple and robust UPLC-SRM/MS method to quantify urinary eicosanoids, Journal of Lipid Research, vol. 23, 2012, pp. 1026-1036.
Hodel, Christian, Myopathy and rhabdomyolysis with lipid-lowering drugs, Toxicology Letters, 128, 2002, pp. 159-168.
European Search Report from European Patent Office for European Patent Application No. 11 18 4669, May 25, 2012, 17 Pages.
Morandi, L. et al., High plasma creatine kinase; review of the literature and proposal for a diagnostic algorithm, Neruol. Sci. (2006) 27:303-311.
Dolegowska, Barbara et al., Lipoxygenase-derived hydroxyeicosatetraenoic acids—novel perioperative markefs of early post-transplant allograft function?, Nephrol. Dial Transplant, (2010) 25L4061-4067.
Gasper, Mason C. et al.. Creatine Kinase: A Review of Its Use in the Diagnosis of Muscle Disease, Medicine and Health, vol. 88, No. 11, Nov. 1, 2005, pp. 399-404.
Oskarsson, B., Myopathy: Five New Things, Neurology, vol. 76, No. 7, Supplement 2, Feb. 15, 2011, pp. S14-S19.
Mammen, Andrew L. et al., Statin myopathy: a review of recent progress, Current Opinion in Rheumatology, vol. 22, No. 6, Nov. 1, 2010, pp. 644-650.
International Search Report and Written Opinion from European Patent Office dated May 29, 2012 issued in International Application No. PCT/EP2012/056478.
Written Opinion of the International Search Report from European Patent Office dated Jan. 31, 2012 issued in International Application No. PCT/EP2011/055569.
Written Opinion of the international Search Report from European Patent Office dated May 25, 2012 for International Application No. PCT/EP2011/055569.
Laaksonen Reijo et al. New Sensitive Biomarkers for Statin-Induced Myopathy. May 2012, 1 Page.
Laaksonen Reijo et al. Predicting Statin Induced Muscle Toxicity. Journal of Clinical Lipidology, Jun. 2011, vol. 5, No. 3, pp. 239-240.
Communication dated Jul. 5, 2013 from European Patent Application No. 11184669.7, pp. 1-6.
Laaksonen, Reijo et al. Sensitive Biomarker for Statin-Induced Myotoxicity. Atherosclerosis Supplements 12, Jun. 2011, No. 1, p. 6.
Laaksonen, Reijo et al. Abstract 14888: Plasma Eicosanoids are Potential Biomarkers for Muscle Weakness and Pain related to Statin Treatment. Circulation, Jun. 2011, 1 Page.
First Office Action and Search Report dated Nov. 27, 2014, Chinese Application No. 201180070668.8, pp. 1-15 (English Translation included).
Japanese Examination Report dated Nov. 4, 2014, Japanese Application No. 2014-503005, pp. 1-3.

BIOMARKERS FOR SENSITIVE DETECTION OF STATIN-INDUCED MUSCLE TOXICITY

CROSS REFERENCE TO RELATED APPLICATIONS

This application is a continuation of International Application PCT/EP2011/055569, filed 8 Apr. 2011 (pending), and claims the benefit of, and relies on the filing date of U.S. provisional patent application No. 61/545,603, filed 11 Oct. 2011, the entire disclosures of which are incorporated herein by reference.

FIELD OF THE INVENTION

This invention relates to methods and uses involving lipid levels to predict or diagnose statin-induced muscle toxicity. The invention is applicable, inter alia, to determining whether a subject requires adjustment of statin treatment and to the evaluation of muscle toxicity induced by new lipid lowering drugs. The methods include analyzing lipid levels of a biological sample, and comparing it to a control.

BACKGROUND OF THE INVENTION

Statins are currently the most widely used lipid-lowering drugs because they reduce the incidence of hard cardiovascular end-points (cardiovascular death, myocardial infarction and stroke) by 25% to 35% in different patient populations. These populations include those with stable or unstable coronary artery disease, diabetics, and hypertensive patients with other risk factors. In general, statins are well tolerated although muscular, liver and gastrointestinal side effects can occur. Statins can be associated with a wide range of muscular side effects, from non-specific or atypical myalgias, to myopathy and the full-blown rhabdomyolysis syndrome.

Myalgias are defined as muscle pain or complaints of sore muscles that can either be generalized or localized. Such symptoms occur in up to 10% of patients and can force physicians to reduce dose, switch to another statin using a trial-and-error approach or stop the medication completely. These muscular symptoms can also contribute to the relatively high rate of patients stopping statin therapy within the first two years of the treatment. Thus, even the more benign muscular symptoms can have important consequences and limit the large clinical and socio-economic benefits potentially offered by these agents.

Myopathy, while less devastating than rhabdomyolysis, can also occur after treatment with statins and is defined as muscle pain and/or weakness with increased creatine kinase (CK) levels at least 10 times the upper limit of normal. The incidence of myopathy is approximately 1-5%. The known predisposing risk factors for statin-related muscle toxicity include renal insufficiency, hypothyroidism, hereditary or acquired muscle diseases, history of muscle toxicity with another statin or a fibrate, concomitant use of a fibric acid derivative, alcohol abuse, clinical settings where increased plasma levels of statins could occur, as well as Asian ancestry.

Rhabdomyolysis is a rare event (well below 0.1% of statin users) but constitutes a life-threatening condition characterized by severe muscle toxicity, large increase in plasma creatine kinase (CK) levels (exceeding 10,000 U/L) and renal insufficiency secondary to myoglobin toxicity. Rhabdomyolysis has caused several patient deaths and has led to the withdrawal of one statin from the market, cerivastatin, (Baycol, Bayer). The incidence of rhabdomyolysis was also recently shown to be increased with another HMG-CoA reductase inhibitor, simvastatin (Zocor, Merck & Co.), when administered at a high dose (A to Z trial).

Currently plasma/serum Creatine kinase (CK) measurement is used as a biomarker for statin-induced muscle toxicity. For the vast majority of cases, CK measurement remains uninformative despite the presence of symptoms. Plasma/serum CK is an unspecific marker because it can be elevated for many other reasons, including physical exercise. An even greater limitation is its poor sensitivity, since it becomes indicative only after a substantial damage to muscle cells involving CK leakage to plasma from tissues. Thus, to this end it is well justified to develop new biomarkers for diagnosis of statin-induced muscle toxicity. Earlier studies (Phillips P S et al.: "*Statin-associated myopathy with normal creatine kinase levels.*" Ann Intern Med. 2002 Oct. 1; 137(7):581-5) on muscle specimens obtained from patients during acute muscle pain have demonstrated, e.g., an accumulation of inflammatory cells in histopathological studies.

The number of lipid mediators in the human body is overwhelming. Attempts have been made to facilitate their identification and quantification by advances in mass spectrometry and lipid biochemistry, which today enable the simultaneous high throughput identification and quantification of hundreds of molecular lipid species in several lipid classes (Ejsing C S, et al: *Global analysis of the yeast lipidome by quantitative shotgun mass spectrometry*. Proc Natl Acad Sci USA 2009, 106:2136-2141; Stahlman M, et al: *High-throughput shotgun lipidomics by quadrupole time-of-flight mass spectrometry*. J Chromatogr B Analyt Technol Biomed Life Sci 2009 Hiukka A, et al: *ApoCIII-enriched LDL in type 2 diabetes displays altered lipid composition, increased susceptibility for sphingomyelinase, and increased binding to biglycan*. Diabetes 2009, 58:2018-2026; Linden D, et al: *Liver-directed overexpression of mitochondrial glycerol-3-phosphate acyltransferase results in hepatic steatosis, increased triacylglycerol secretion and reduced fatty acid oxidation*. FASEB J 2006, 20:434-443.) collectively referred to as the lipidome. Lipidomic studies have sought to identify lipid cellular distribution and to describe their biochemical mechanisms, interactions and dynamics. Lipidomics is capable in principle of quantifying the exact chemical composition of lipidomes (Han X, Gross R W: *Global analyses of cellular lipidomes directly from crude extracts of biological samples by ESI mass spectrometry: a bridge to lipidomics*. J Lipid Res 2003, 44:1071-1079).

The bulk of the lipid data in the art today presents lipids in a sum composition format, i.e., phosphatidylcholine (PC) 34:1 (Brugger B, et al: *Quantitative analysis of biological membrane lipids at the low picomole level by nano-electrospray ionization tandem mass spectrometry*. Proc Natl Acad Sci USA 1997, 94:2339-2344) where the molecular lipid and the attached fatty acid tails remain unidentified. The identification of molecular lipid species, e.g., PC 16:0/18:1 (Ekroos K, et al: *Charting molecular composition of phosphatidylcholines by fatty acid scanning and ion trap MS*3 *fragmentation*. J Lipid Res 2003, 44:2181-2192) is the main feature of advanced lipidomics, which delivers highly resolved molecular lipid species rather than summed fatty acid information. For example, the information of the type of fatty acids and their positions of attachment to the glycerol backbone making up the particular PC molecule is revealed. There are conventional techniques such as thinlayer chromatography combined with gas chromatography but they not only require considerably larger sample amounts and laborious sample preparation, but they do not deliver the molecular lipid species. Despite multiple mass spectrometry techniques capable of characterizing lipid entities, most of them are still unable to deliver reliable high-quality quantitative data in terms of absolute or close-to absolute concentrations.

There is a need for specific and reliable methods for the detection and diagnosis of statin-induced muscle toxicity, as well as markers useful in this regard. There is also a need for improvements of existing treatment regimes with statins or lipid lowering drugs.

SUMMARY OF THE INVENTION

The present invention inter alia provides novel lipidomic markers, also referred to herein as "biomarkers", for the detection and diagnosis of statin-induced muscle toxicity, such as statin-induced muscle toxicity associated with muscle disease, muscle dystrophy, myalgia, myositis, myopathy or rhabdomyolysis.

In one aspect of the present invention, methods, lipidomic markers, agents such as antibodies and kits are inter alia disclosed and/or claimed herein for detecting statin associated muscular side effects, from non-specific or atypical myalgias to myopathy and the full-blown rhabdomyolysis syndrome. Myalgias are defined as muscle pain or complaints of sore muscles that can either be generalized or localized. Myopathy, while less catastrophic than rhabdomyolysis, can also occur after treatment with statins and is defined as muscle pain and/or weakness with increased CK levels at least 10 times the upper limit of normal.

Methods according to the invention may, e.g., comprise the steps of: a) providing a biological sample from a subject being treated, to be treated, or having been treated with a statin; b) determining the concentration(s) of one or more lipid(s) and/or lipid-lipid concentration ratio(s) identified herein as useful lipidomic markers in accordance with the invention in said sample; and c) comparing said determined lipid concentration(s) and/or lipid-lipid concentration ratio(s) to the corresponding lipid concentration(s) and/or to (a) lipid ratio(s) in a control.

The lipidomic markers of the present invention allow for sensitive detection of statin-induced muscle toxicity. It will be appreciated that the same applies to the complications of statin-induced muscle toxicity. This will facilitate improving patient care, lessening symptom development and suffering, and achieving decreased morbidity/mortality associated with statin side-effects. Thus, the lipidomic markers described and claimed herein allow for individual tailoring of drug intervention regarding patients treated, or to be treated, with statins. Also, the invention is applicable to animal experiments where statins and statin-like compounds are tested. The invention will inter alia allow a better safety assessment of novel lipid lowering medications to be made.

The lipidomic markers may be eicosanoids, ceramides or cerebrosides. Moreover, the lipidomic markers are selected from the lipid classes of ceramides, lactosylceramides, galactosyl- or glucosylceramides, globotriaosylceramides (Gb3), hydroxyeicosatetraenoic acids (HETE), dihydroxyeicosatrienoic acids (DHET), hydroxyeicosapentaenoic acids (HEPE) and/or prostaglandins. The lipidomic marker may also be a metabolic product of 12/15-lipoxygenase or a metabolic product of cyclooxygenase-2.

Accordingly, a method is inter alia provided herein for determining whether a subject is at risk to develop, or is suffering from statin-induced muscle toxicity and/or one or more of its complications, comprising determining in a sample from said subject the concentration(s) of one or more lipid(s), wherein (an) increased or decreased concentration(s) in said sample, when compared to a control, is (are) indicative of said subject suffering from said statin-induced muscle toxicity and/or said complication(s), wherein the one or more lipid(s) whose increase in concentration is (are) compared to the control is (are) selected from: 12-HETE, LacCer(d18:1/22:0), 15-HETE, Gb3(d18:1/24:1), Gb3(d18:1/22:0), Gb3(d18:1/24:0), LacCer(d18:1/24:0), AA, Total eicosanoids, Total Gb3, Cer(d18:1/20:0), Gb3 (d18:1/20:0), 12-HEPE, PGE2, LacCer(d18:1/20:0), 12-OXOETE, 17-HDOoHE, PGD2, TXB3, PS 18:0/18:1, SM (d18:1/24:2) and LacCer(d18:1/24:1) (see Tables 3 and 4); and wherein the one or more lipid(s) whose decrease in concentration is (are) compared to the control is (are) selected from: Gb3(d18:1/16:0), Gb3(d18:1/18:0), 14_15-DHET, and 8_9-DHET (see Table 3).

Alternatively, a method is provided herein for determining whether a subject is at risk to develop, or is suffering from statin-induced muscle toxicity and/or one or more of its complications, comprising determining in a sample from said subject one or more lipid-lipid concentration ratio(s), wherein (an) increased or decreased lipid-lipid concentration ratio(s) in said sample, when compared to a control, is (are) indicative of said subject suffering from said statin-induced muscle toxicity and/or said complication(s), wherein the one or more lipid-lipid concentration ratio(s) whose increase is (are) compared to the control is (are) selected from: 12-HETE/15-HETrE, 12-HETE/14_15-DHET, 12-HETE/Gb3(d18:1/16:0), 12-HETE/Glc/GalCer (d18:1/24:1), 12-HETE/Glc/GalCer(d18:1/18:0), Gb3(d18:1/24:1)/LacCer(d18:1/16:0), LacCer(d18:1/22:0)/LacCer (d18:1/24:1), Cer(d18:1/20:0)/Glc/GalCer(d18:1/24:1) (Table 6); and wherein the one or more lipid-lipid concentration ratio(s) whose decrease is (are) compared to the control is (are) selected from LacCer(d18:1/16:0)/LacCer (d18:1/22:0), Gb3(d18:1/16:0)/Gb3(d18:1/24:1) and 11-HETE/12-HETE (Table 6).

Another aspect of the invention, provided herein is a method for determining whether a subject is at risk to develop, or is suffering from statin-induced muscle toxicity and/or one or more of its complications, wherein the subject is female, comprising determining in a sample from said subject the concentration(s) of one or more lipid(s), wherein (a) decreased concentration(s) in said sample, when compared to a control, is (are) indicative of said subject suffering from said statin-induced muscle toxicity and/or said complication(s), wherein the one or more lipid(s) whose decrease in concentration is (are) compared to the control is (are) selected from: Total LacCer, LacCer(d18:1/16:0) and Glc/GalCer(d18:1/24:1) (see Table 3).

In a preferred embodiment, the one or more lipid(s) whose increase in concentration is (are) compared to the control is (are) selected from: 12-HETE, LacCer(d18:1/22:0) and Gb3 (d18:1/24:1) (see Table 5).

In another preferred embodiment, wherein the subject is female, the one or more lipid(s) whose decrease in concentration is (are) compared to the control is (are) selected from: LacCer(d18:1/16:0) and Glc/GalCer(d18:1/24:1) (see Table 5).

In another aspect, the present invention relates to a method for determining whether the statin treatment and/or the treatment with a lipid lowering drug of a subject needs adjustment, comprising determining in a sample from said subject the concentration(s) of one or more lipid(s), wherein (an) increased or decreased concentration(s) in said sample, when compared to a control, is (are) indicative of said treatment requiring adjustment, wherein the one or more lipid(s) whose increase in concentration is (are) compared to the control is (are) selected from: 12-HETE, LacCer(d18:1/22:0), 15-HETE, Gb3(d18:1/24:1), Gb3(d18:1/22:0), Gb3 (d18:1/24:0), LacCer(d18:1/24:0), AA, Total eicosanoids, Total Gb3, Cer(d18:1/20:0), Gb3(d18:1/20:0), 12-HEPE, PGE2, LacCer(d18:1/20:0), 12-OXOETE, 17-HDOoHE, PGD2, TXB3, PS 18:0/18:1, SM (d18:1/24:2) and LacCer (d18:1/24:1) (see Tables 3 or 4); and wherein the one or more lipid(s) whose decrease in concentration is (are) compared to the control is (are) selected from: Gb3(d18:1/16:0), Gb3(d18:1/18:0), 14_15-DHET and 8_9-DHET (see Table 3).

In another aspect, the present invention relates to a method for determining whether the statin treatment and/or the treatment with a lipid lowering drug of a subject needs adjustment, comprising determining in a sample from said subject one or more lipid-lipid concentration ratio(s), wherein (an) increased or decreased lipid-lipid concentration ratio(s) in said sample, when compared to a control, is (are) indicative of said treatment requiring adjustment, wherein the one or more lipid-lipid concentration ratio(s) whose increase is (are) compared to the control is (are) selected from: 12-HETE/15-HETrE, 12-HETE/14_15-DHET, 12-HETE/Gb3(d18:1/16:0), 12-HETE/Glc/GalCer(d18:1/24:1), 12-HETE/Glc/GalCer(d18:1/18:0), Gb3(d18:1/24:1)/LacCer(d18:1/16:0), LacCer(d18:1/22:0)/LacCer (d18:1/24:1), Cer(d18:1/20:0)/Glc/GalCer(d18:1/24:1) (Table 6); and wherein the one or more lipid-lipid concentration ratio(s) whose decrease is (are) compared to the control is (are) selected from LacCer(d18:1/16:0)/LacCer (d18:1/22:0), Gb3(d18:1/16:0)/Gb3(d18:1/24:1) and 11-HETE/12-HETE (Table 6).

Yet in another aspect, the present invention relates to a method for determining whether the statin treatment and/or the treatment with a lipid lowering drug of a subject needs adjustment; wherein the subject is female, comprising determining in a sample from said subject the concentration(s) of one or more lipid(s), wherein (a) decreased concentration(s) in said sample, when compared to a control, is (are) indicative of said treatment requiring adjustment, wherein the one or more lipid(s) whose decrease in concentration is (are) compared to the control is (are) selected from: Total LacCer, LacCer(d18:1/16:0) and Glc/GalCer(d18:1/24:1) (see Table 3).

In a preferred embodiment, the one or more lipid(s) whose increase in concentration is (are) compared to the control is (are) selected from: 12-HETE, LacCer(d18:1/22:0) and Gb3 (d18:1/24:1) (see Table 5).

In another preferred embodiment, wherein the subject is female, the one or more lipid(s) whose decrease in concentration is (are) compared to the control is (are) selected from: LacCer(d18:1/16:0) and Glc/GalCer(d18:1/24:1) (see Table 5).

For the purpose of the method for determining whether the statin treatment or the treatment with lipid lowering drug of a subject needs adjustment, the adjustment of said statin treatment may comprise (a) a reduction of statin dose; (b) a cessation of statin treatment; (c) a re-commencement of statin treatment; (d) a change to a different statin drug; (e) a change to a different lipid lowering drug; or (f) a cessation of another drug treatment which led to muscle toxicity due to its interaction with one or more statins.

In a further embodiment, the methods of the invention may be used for evaluating the degree of muscle toxicity induced by a novel statin or a novel lipid lowering medication in a subject undergoing treatment with said statin or lipid lowering medication.

The methods of the invention may be used for determining early warning signs of muscle toxicity in said subject.

In addition, or alternatively, the methods may be used for determining whether the symptoms of muscle toxicity found in a subject are due to statin-induced muscle toxicity.

For the purposes of the methods of the invention, at least one lipid concentration from Tables 3 or 4 or lipid-lipid concentration ratio from Table 6 may be determined to assess whether a subject is at risk to develop, or is suffering from statin-induced muscle toxicity and/or one or more of its complications, or to determine whether the statin treatment or treatment with a lipid lowering drug of a subject needs adjustment. However, it is also possible, and may be advantageous, to determine at least 2, at least 3, at least 4, at least 5, at least 6, at least 7, or at least 8 lipid concentrations from Tables 3 or 4, or at least 2, at least 3, at least 4, at least 5, at least 6, at least 7, or at least 8 lipid-lipid concentration ratios from Table 6. Where more than one lipidomic marker is determined and used for the assessment, it may be advantageous that a specific lipid concentration or lipid-lipid concentration ratio is given greater weight than others in the above-mentioned assessment.

The methods of the invention encompass the determination of (a) lipid concentration(s) or (a) lipid-lipid concentration ratio(s) in a sample from a subject that is being treated with one or more statins.

Alternatively, the methods of the invention encompass the determination of (a) lipid concentration(s) or (a) lipid-lipid concentration ratio(s) in a sample from a subject that had undergone statin treatment, but discontinued said treatment, e.g., due to onset of muscle pain.

In a further alternative, the methods of the invention encompass the determination of (a) lipid concentration(s) or (a) lipid-lipid concentration ratio(s) in a sample from a subject that has not yet been treated with statins.

The methods of the invention may further encompass the determination of (a) lipid concentration(s) or (a) lipid-lipid concentration ratio in a sample from a subject that is at a high risk for developing statin-induced muscle toxicity and/or one or more of its complications.

For the purposes of the methods of the invention, a comparison of the subject's sample is made in respect of a control.

In a preferred embodiment, the control is, for example, a control sample, preferably a control sample that corresponds to the subject's sample.

In a preferred embodiment, the control sample is from the same subject undergoing statin treatment, but prior to the onset of muscle toxicity. The control may, however, also be a sample from the same subject prior to statin treatment or during discontinuation of statin treatment. In another preferred embodiment, it may also be from another subject with no signs or history of statin-induced muscle toxicity.

In another preferred embodiment, the control is a control sample from a population of subjects with no signs or history of statin-induced muscle toxicity.

In yet another preferred embodiment, however, the control is not a sample but merely a control value established from one or more subject(s) not on statin treatment and with no signs or history of muscle toxicity. Alternatively, the control may advantageously be a control value established from one or more subject(s) on statin treatment and with no signs or history of muscle toxicity.

In accordance with the present invention, the concentration(s) of the individual lipid(s) and/or the lipid-lipid concentration ratio(s) of lipids in the sample from the subject are preferably compared to the concentration(s) of the corresponding lipid(s) or to (a) lipid ratio(s) (e.g., the corresponding lipid-lipid concentration ratio(s)) in the control, be it a control sample or a control value, for determining whether a subject is at risk to develop, or is suffering from statin-induced muscle toxicity (and/or one or more of its complications), or to determine whether the statin treatment or treatment with a lipid lowering drug of a subject needs adjustment. Some illustrative examples of the comparisons that can be made between a subject's sample and a control are shown in the table below:

TABLE 1

Example on comparison pairs between a subject's sample and a control.

Comparison pairs

| | Case | Control | Readout |
|---|---|---|---|
| 1 | Subject on Statin with muscle toxicity or a high risk subject on statin with no muscle toxicity | Subject(s) on Statin with no muscle toxicity | Increase or decrease in concentration of lipid(s) in Tables 3 or 4 |
| 2 | Subject on Statin with muscle toxicity | Same subject on statin prior to muscle toxicity | Increase or decrease in concentration of lipid(s) in Tables 3 or 4 |
| 3 | Subject on Statin with muscle toxicity | Same subject prior to statin therapy | Change or lack of change in concentration of lipid(s) in Tables 3 or 4 e.g., a) increased concentration of 12-HETE, b) decreased concentration of "decreased" lipids, c) lack of change in remaining lipids |
| 4 | Subject on statin with muscle toxicity | Same subject after statin withdrawal | Change or lack of change in concentration of lipid(s) in Tables 3 or 4 e.g., a) increased concentration of 12-HETE, b) decreased concentration of "decreased" lipids, c) lack of change in remaining lipids |

On the other hand, the comparison in accordance with the present invention of the concentration(s) of the individual lipid(s) or lipid-lipid concentration ratio(s) in the sample from said subject may also be made to the concentration(s) or concentration ratio(s) of (an)other individual molecule(s) in the control, again either control sample or control value, for determining whether a subject is at risk to develop, or is suffering from statin-induced muscle toxicity (and/or one or more of its complications), or to determine whether the statin treatment or treatment with a lipid lowering drug of a subject needs adjustment. Such other individual molecule(s) in the control is (are) preferably molecule(s) where the concentration(s) or concentration ratio(s) thereof is (are) similar, or essentially similar, in all or at least a majority of subjects, so that the concentration(s) or concentration ratio(s) is (are) suitable as point of reference for determining whether there is an increase or decrease in said sample in respect of the lipidomic markers according to the invention. Preferred in this regard is/are, for example, (an)other lipid(s). Also preferred in this regard is/are, for example, (a) protein(s). Particularly preferred in this regard is/are (a) molecule(s) in the control that is/are regularly measured in a clinical setting. For example, preferred are embodiments where the comparison is made to the concentration of apoA, apoB, albumin or total PC in the control (again control sample or control value), or combinations thereof.

In a further embodiment, the methods of the invention may further comprise determining or evaluating the level of creatine kinase (CK) in the subject or in a sample from the subject. In one embodiment of the invention, the subject has elevated creatine kinase levels. In another embodiment of the invention, the subject does not have elevated creatine kinase levels.

In accordance with the methods of the invention, the sample can be blood plasma, blood serum, or muscle biopsy tissue. The sample may also be a fraction of blood, blood plasma or blood serum, e.g., a lipoprotein fraction. A blood sample can be prepared and plasma or serum, or fractions thereof, can be separated therefrom with techniques well known to the person skilled in the art. Alternatively, both the sample from the subject and the control sample may also be a urine sample or a tissue sample, e.g., muscle biopsy tissue.

Collecting information on a lipidomic marker (i.e., a lipid concentration or lipid-lipid concentration ratio, as described and claimed herein) according to the methods of the present invention from the subject's sample, and also from the control sample, can be performed via various chemical and high resolution analytical techniques. Particularly suitable analytical techniques include, but are not limited to, mass spectrometry and nuclear magnetic resonance spectroscopy. Indeed, any high resolution technique capable of resolving individual lipids or lipid classes and providing structural information of the same can be used to determine the lipidomic markers according to the invention from the subject's sample, and also from the control sample. For the purposes of the methods of the present invention the lipid concentration(s) or lipid-lipid concentration ratio(s) are thus preferably determined by using mass spectrometry. However, nuclear magnetic resonance spectroscopy, fluorescence spectroscopy or dual polarisation interferometry, high performance separation methods such as HPLC or HPLC, an immunoassay such as an ELISA and/or the use of a binding moiety capable of specifically binding the lipid analyte are also useful in this regard.

As indicated above, according to an alternative or further embodiment of the methods of the invention, a lipid analyte in a sample can be detected and/or quantified by combining the analyte with a binding moiety capable of specifically binding the analyte. The binding moiety can include, for example, a member of a ligand-receptor pair, i.e., a pair of molecules capable of having a specific binding interaction. The binding moiety can also include, for example, a member of a specific binding pair, such as antibody-antigen, enzyme-substrate, nucleic acid-based ligands, other protein ligands, or other specific binding pairs known in the art.

In a particularly preferred embodiment, the lipidomic markers of the present invention are determined with mass spectrometry (MS), wherein the MS instrument is optionally coupled to direct infusion methods and/or high performance separation methods such as HPLC or HPLC. The amount of the individual lipids or lipid classes in the collected lipidomic markers is used when comparing the collected lipid profile to a control.

In another aspect of the present invention, an agent capable of binding to any one of the lipids in Tables 3, 4 or 6, is used for predicting, diagnosing, preventing or treating statin-induced muscle toxicity and/or one or more of its complications in a subject. Similarly, the present invention relates to a method of predicting, diagnosing, preventing or treating statin-induced muscle toxicity and/or one or more of its complications in a subject using, or administering a therapeutically effective amount of an agent that binds to any one of the lipids in Tables 3, 4 or 6. In a preferred embodiment, the said agent is an antibody.

For example, since 12/15-lipoxygenase or cyclooxygenase-2 derived metabolites may be related to pain signaling (Mathie A. *Ion channels as novel therapeutic targets in the treatment of pain. J Pharm Pharmacol.* 2010 September; 62(9):1089-95; Ma W, Quirion R. *Does COX2-dependent PGE2 play a role in neuropathic pain? Neurosci Lett.* 2008 Jun. 6; 437(3):165-9; Xie C, Wang D H. *Inhibition of Renin Release by Arachidonic Acid Metabolites, 12(s)-HPETE and 12-HETE: Role of TRPV1 Channels. Endocrinology.* 2011 October; 152(10):3811-9), inhibition of one or both of these metabolic pathways with an agent may offer (an) efficient mechanism(s) for treating or preventing statin-induced muscle toxicity or muscle pain caused by statin induced muscle toxicity.

Ceramides are known to activate cytosolic phospholipase A2 (cPLA2), which leads to increased 12-HETE levels through the release of arachidonic acid from phospholipids (Pettus B J, Bielawska A, Subramanian P, Wijesinghe D S, Maceyka M, Leslie C C, Evans J H, Freiberg J, Roddy P, Hannun Y A, Chalfant C E. *Ceramide 1-phosphate is a direct activator of cytosolic phospholipase A2. J Biol Chem.* 2004 Mar. 19; 279(12):11320-6. Epub 2003 Dec. 15; Farooqui A A, Horrocks L A. *Phospholipase A2-generated lipid mediators in the brain: the good, the bad, and the ugly. Neuroscientist.* 2006 June; 12(3):245-60; Nanda B L, Nataraju A, Rajesh R, Rangappa K S, Shekar M A, Vishwanath B S. *PLA2 mediated arachidonate free radicals: PLA2 inhibition and neutralization of free radicals by anti-oxidants—a new role as anti-inflammatory molecule. Curr Top Med Chem.* 2007; 7(8):765-77). Since the present invention shows that ceramides and 12-HETE are upregulated in statin-induced muscle toxicity, inhibition of ceramide synthesis and/or arachidonic acid production with an agent may also be useful in treating or preventing statin-induced muscle toxicity or muscle pain caused by statin induced muscle toxicity. For example, as eicosanoids are involved in arachidonic acid metabolism (Zeldin, D C. *Epoxygenase Pathways of Arachidonic Acid Metabolism. JBC.* 2001. 276 (39):36059-36062), they may be an appropriate target for an agent to inhibit statin-induced muscle toxicity. In one preferred embodiment of the invention, an agent capable of binding to any one of the eicosanoids of the present invention (e.g., 12-HETE, 15-HETE, AA, 14_15-DHET, 8_9-DHET (Table 3), 12-HEPE, PGE2,12-OXOETE, 17-HDoHE, PGD2 or TXB3 (Table 4) is used for predicting, diagnosing, preventing or treating statin-induced muscle toxicity and/or one or more of its complications in a subject. Similarly, the present invention relates to a method of predicting, diagnosing, preventing or treating statin-induced muscle toxicity and/or one or more of its complications in a subject using, or administering a therapeutically effective amount of an agent that binds to any one of the eicosanoids of the present invention (e.g., 12-HETE, 15-HETE, AA, 14_15-DHET, 8_9-DHET (Table 3), 12-HEPE, PGE2,12-OXOETE, 17-HDoHE, PGD2 or TXB3 (Table 4). In a preferred embodiment, the said agent is an antibody.

Alternatively, the present invention relates to an agent for use in preventing or treating statin-induced muscle toxicity and/or one or more of its complications in a subject, wherein the agent affects the activity, functionality or concentration of an enzyme, wherein said enzyme catalyzes a reaction that produces or degrades any one of the lipids in Tables 3, 4 or 6. Similarly, the present invention relates to a method of preventing or treating statin-induced muscle toxicity and/or one or more of its complications in a subject using, or administering an agent, wherein the agent affects the activity, functionality or concentration of an enzyme, wherein said enzyme catalyzes a reaction that produces or degrades any one of the lipids in Tables 3, 4 or 6.

Also encompassed by the present invention is a kit for predicting statin-induced muscle toxicity and/or one or more of its complications, or for performing the methods or uses described and/or claimed herein, wherein the kit comprises reagents and reference compounds. The reference compounds may be one or more of the following, but are not limited to: (a) (a) lipid standard(s) chosen from the lipids in Tables 3, 4 or 6, (b) one Or more control markers (for example, a lipid or lipids, preferably a lipid corresponding to any of the lipidomic markers described and/or claimed herein, or (an)other lipid(s), e.g., total PC, or another molecule, e.g., a protein; c) positive and/or negative controls; d) internal and/or external standards; e) calibration line controls; (f) an antibody or other binding moiety capable of binding any one of the lipids in Tables 3, 4 or 6. The reagents are solution(s), solvent(s), and/or buffer(s) useful for performing said methods or uses.

In one embodiment of the invention, a kit is provided for predicting statin-induced muscle toxicity and/or one or more of its complications, or for performing the methods of the invention, wherein the kit comprises (a) (a) lipid standard(s) chosen from the lipids in Tables 3, 4 or 6, and optionally one or more further reference compound(s) selected from: (b) one or more control markers (for example, a lipid or lipids, preferably a lipid corresponding to any of the lipidomic markers described and/or claimed herein, or another lipid(s), e.g., total PC, or another molecule, e.g., a protein); c) positive and/or negative controls; d) internal and/or external standards, which may or may not be chemically modified, tagged or non-endogenous occurring molecules in human; e) calibration line controls; and (f) an agent, optionally an antibody, capable of binding any one of the lipids in Tables 3, 4 or 6, and (g) (a) reagent(s) for performing said methods or uses.

Preferred kits according to the invention comprise, for example, the following combinations of the above listed constituents: (a) and (b), and optionally (g); (a) and (c), and optionally (g); (a) and (d), and optionally (g); (a) and (e), and optionally (g); (a) and (f), and optionally (g); (a), (b) and (c), and optionally (g); (a), (c) and (d), and optionally (g); (a), (d) and (e), and optionally (g); or (a), (e) and (f), and optionally (g).

In one preferred embodiment, the one or more control marker(s) of the claimed kit is/are (a) molecule(s) that is/are regularly measured in a clinical setting. For example, preferred are embodiments wherein the one or more said control marker(s) is CK.

In a preferred embodiment, the kit is used to predict statin-induced muscle toxicity and/or one or more of its complications, or to perform any of the methods encompassed by the present invention, wherein the lipid concentration(s) or lipid-lipid concentration ratio(s) in a sample from a subject is (are) determined by using mass spectrometry. The sample may be subjected to a purification and/or other sample pre-preparation step(s) before mass spectrometry analysis. The purification step may be, but is not limited to chromatography, for example, high performance liquid chromatography (HPLC) and/or ultra high performance liquid chromatography (UHPLC). The sample pre-preparation step may be, but is not limited to solid-phase extraction (SPE), derivatization and/or liquid-liquid extraction. The said mass spectrometry determination may be done by tandem mass spectrometry.

In another aspect, the present invention relates to a statin or a lipid lowering drug for use in the treatment of a subject at risk to develop or suffering from atherosclerosis or cardiovascular disease (CVD) and/or one or more of their complications, wherein said subject would be identified as being at risk to develop or as suffering from statin-induced muscle toxicity when applying any of the methods, agents, kits or uses described and/or claimed herein. Similarly, the present invention relates to a method of treating a subject at risk to develop or suffering from atherosclerosis or cardiovascular disease (CVD) and/or one or more of their complications with a statin or a lipid lowering drug, wherein said subject would be identified as being at risk to develop or as suffering from statin-induced muscle toxicity when applying any of the methods, agents, kits or uses described and/or claimed herein.

In a further embodiment, the present invention relates to a statin or a lipid lowering drug for use in the treatment of a subject at risk to develop or suffering from atherosclerosis or cardiovascular disease (CVD) and/or one or more of their complications, wherein said subject actually has been identified as being at risk to develop or as suffering from statin-induced muscle toxicity by any of the methods, agents, kits or uses described and/or claimed herein. Similarly, the present invention relates to a method of treating a subject at risk to develop or suffering from atherosclerosis or cardiovascular disease (CVD) and/or one or more of their complications with a statin or a lipid lowering drug, wherein said subject actually has been identified as being at risk to develop or as suffering from statin-induced muscle toxicity by any of the methods, agents, kits or uses described and/or claimed herein.

In yet another aspect, the present invention relates to a statin or a lipid lowering drug for use in the treatment of a subject at risk to develop or suffering from atherosclerosis or cardiovascular disease (CVD) and/or one or more of their complications, wherein said subject would be identified as not being at risk to develop or as not suffering from statin-induced muscle toxicity when applying any of the methods, agents, kits or uses described and/or claimed herein. Similarly, the present invention relates to a method of treating a subject at risk to develop or suffering from atherosclerosis or cardiovascular disease (CVD) and/or one or more of their complications with a statin or a lipid lowering drug, wherein said subject would be identified as not being at risk to develop or as not suffering from statin-induced muscle toxicity when applying any of the methods, agents, kits or uses described and/or claimed herein.

In a further embodiment, the present invention relates to a statin or a lipid lowering drug for use in the treatment of a subject at risk to develop or suffering from atherosclerosis or cardiovascular disease (CVD) and/or one or more of their complications, wherein said subject actually has been identified as not being at risk to develop or as not suffering from statin-induced muscle toxicity by any of the methods, agents, kits or uses described and/or claimed herein. Similarly, the present invention relates to a method of treating a subject at risk to develop or suffering from atherosclerosis or cardiovascular disease (CVD) and/or one or more of their complications with a statin or a lipid lowering drug, wherein said subject actually has been identified as not being at risk to develop or as not suffering from statin-induced muscle toxicity by any of the methods, agents, kits or uses described and/or claimed herein.

In yet another aspect, the present invention relates to a statin or a lipid lowering drug for use in the treatment of a subject at risk to develop or suffering from atherosclerosis or cardiovascular disease (CVD) and/or one or more of their complications, wherein said treatment is, or has been, assessed using any of the methods for determining the need for treatment adjustment described and/or claimed herein, and wherein said treatment is, or has been, adjusted accordingly. Similarly, the present invention relates to a method of treating a subject at risk to develop or suffering from atherosclerosis or cardiovascular disease (CVD) and/or one or more of their complications with a statin or a lipid lowering drug, wherein said treatment is, or has been, assessed using any of the methods for determining the need for treatment adjustment described and/or claimed herein, and wherein optionally, said treatment is, or has been, adjusted accordingly. In connection with this aspect of the invention, such adjustment may suitably comprise, but is not limited to: (a) a reduction of statin dose; (b) a cessation of statin treatment; (c) a re-commencement of statin treatment; (d) a change to a different statin drug; (e) a change to a different lipid lowering drug; or (f) a cessation of another drug treatment which led to muscle toxicity due to its interaction with one or more statins.

In the context of all aspects and embodiments of the invention described and claimed herein, a statin may be one selected from, but not limited to, the group consisting of atorvastatin, cerivastatin, fluvastatin, fluvastatin XL, lovastatin, pitavastatin, pravastatin, rosuvastatin and/or simvastatin.

In the context of all aspects and embodiments of the invention described and claimed herein, the determination of the lipid concentration(s) or lipid-lipid concentration ratio(s) is typically performed using an assay.

In the context of all aspects and embodiments of the invention described and claimed herein, muscle toxicity may be associated with a muscle disease, for example, a muscle dystrophy.

In the context of all aspects and embodiments of the invention described and claimed herein, statin-induced muscle toxicity complications include in particular those selected from myalgia, myositis, myopathy and rhabdomyolysis. Statin myopathy or myositis is typically characterized by muscle pain (myalgia), muscle weakness, joint pain or rhabdomyolysis.

DETAILED DESCRIPTION OF THE INVENTION

The present invention is the result of applying lipidomics to the identification of biomarkers indicative of statin-induced muscle toxicity. It will facilitate the mission of making sure the right individual receives the right statin or cholesterol lowering drug at the right time and dose, thereby opening this therapeutic area towards personalizing hitherto more generally applied medicines and/or treatment regimes.

Due to both high sensitivity and specificity of lipidomics, even the smallest sample amounts can be analyzed.

According to the present invention, the lipids may be analyzed by a variety of techniques. In the context of the present invention, electrospray ionization mass spectrometry-based lipidomics is the preferred technology. The superior quality and specificity of shotgun and targeted analysis methods will meet stringent regulatory standards, such as good laboratory practice guidelines (GLP) when set-up in the proper environment.

As used herein, muscle toxicity is an adverse change in muscle cell(s) and/or muscle tissue induced by a drug.

As used herein, myopathy is a general term referring to any disease of muscles; myopathies can be acquired or inherited and can occur at birth or later in life (Source: NINDS Myopathy Page-http://accessible.ninds.nih.gov/health_and_medical/disorders/myopathy.htm).

As used herein, myalgia is a term that describes muscle ache or weakness without creatine kinase (CK) elevation.

As used herein, myositis is a term to describe muscle symptoms with increased CK levels.

Rhabdomyolysis as used herein is characterized by muscle symptoms with marked CK elevation (typically substantially greater than 10 times the upper limit of normal [ULM]) and with creatinine elevation (usually with brown urine and urinary myoglobin).

A muscle disease as used herein is any disease or disorder that affects the muscle system.

A muscle dystrophy as used herein is a hereditary muscle disease that weakens the muscles.

Muscular dystrophies are characterized by progressive skeletal muscle weakness, defects in muscle proteins, and the death of muscle cells and tissue. Muscle dystrophies may include Duchenne, Becker, limb girdle, congenital, facioscapulohumeral, myotonic, oculopharyngeal, distal, and/or Emery-Dreifuss diseases.

As used herein, a complication of atherosclerosis or CVD includes in particular a complication selected from myocardial infarction (MI), AMI, angina pectoris, transient ischemic attack (TIA), stroke and death.

Some abbreviations used herein have the following meaning: CK is creatine kinase, ADR is adverse drug reaction, MS is mass spectrometry, HPLC is high performance liquid chromatography, and HPLC is ultra high performance liquid chromatography, ROC is receiving operating characteristics, and AUC is area under curve.

Moderate to severe creatine kinase elevations are those considered greater than 10 times ULN or greater than 10,000 IU/L. Mild CK elevation is considered to be greater than the ULN but less than 10 times the ULN (Jacobson T A, et al: *Toward "Pain-Free" Statin Prescribing: Clinical Algorithm for Diagnosis and Management of Myalgia. Mayo Clin Proc. June* 2008; 83(6):687-700; Joy T R and Hegele R A, *Narrative review: statin-related myopathy. Ann Intern Med.* 2009 Jun. 16; 150(12):858-68).

A statin and a statin treatment, respectively, in accordance with the present invention will preferably be the following statins and treatments therewith, respectively: cerivastin (0.4 mg/d, Phillips P S et al: *Statin-Associated Myopathy with Normal Creatine Kinase Levels. Ann Intern Med.* 2002; 137:581-585; Evans M and Rees A: *The myotoxicity of statins. Current Opinion in Lipidology.* 2002, 13:415-420); fluvastatin (80 mg/d, Jacobson T A, et al: *Toward "Pain-Free" Statin Prescribing:Clinical Algorithm for Diagnosis and Management of Myalgia. Mayo Clin Proc. June* 2008; 83(6):687-700); fluvastatin XL (80 mg/d, Jacobson T A, et al: *Toward "Pain-Free" Statin Prescribing:Clinical Algorithm for Diagnosis and Management of Myalgia. Mayo Clin Proc. June* 2008; 83(6):687-700); lovastatin (40 mg/d, Phillips P S et al: *Statin-Associated Myopathy with Normal Creatine Kinase Levels. Ann Intern Med.* 2002; 137:581-585); pravastatin (40 mg/d, Phillips P S et al: *Statin-Associated Myopathy with Normal Creatine Kinase Levels. Ann Intern Med.* 2002; 137:581-585; Jacobson T A, et al: *Toward "Pain-Free" Statin Prescribing:Clinical Algorithm for Diagnosis and Management of Myalgia. Mayo Clin Proc. June* 2008; 83(6):687-700); rosuvastatin (2.5 to 20 mg, 1 to 7 times weekly, with a preferred embodiment of 5 or 10 mg per day, Joy T R and Hegele R A, *Narrative review: statin-related myopathy. Ann Intern Med.* 2009 Jun. 16; 150(12):858-68); Jacobson T A, et al: *Toward "Pain-Free" Statin Prescribing:Clinical Algorithm for Diagnosis and Management of Myalgia. Mayo Clin Proc. June* 2008; 83(6):687-700); atorvasatin (10 or 20 mg/d, Phillips P S et al: *Statin-Associated Myopathy with Normal Creatine Kinase Levels. Ann Intern Med.* 2002; 137:581-585); 40 mg/d (Laaksonen R, et al: *A Systems Biology Strategy Reveals Biological Pathways and Plasma Biomarker Candidates for Potentially Toxic Statin-Induced Changes in Muscle. PLoS ONE.* December 2006, Issue 1, e97: 1-9); 40 or 80 mg/d (Jacobson T A, et al: *Toward "Pain-Free" Statin Prescribing:Clinical Algorithm for Diagnosis and Management of Myalgia. Mayo Clin Proc. June* 2008; 83(6):687-700); and/or simvastatin (40 or 80 mg/d, Phillips P S et al: *Statin-Associated Myopathy with Normal Creatine Kinase Levels. Ann Intern Med.* 2002; 137:581-585); 80 mg/d (Laaksonen R, et al: *A Systems Biology Strategy Reveals Biological Pathways and Plasma Biomarker Candidates for Potentially Toxic Statin-Induced Changes in Muscle. PLoS ONE.* December 2006, Issue 1, e97: 1-9; Jacobson T A, et al: *Toward "Pain-Free" Statin Prescribing: Clinical Algorithm for Diagnosis and Management of Myalgia. Mayo Clin Proc. June* 2008; 83(6):687-700). Alternatively, fluvastatin, lovastatin, pravastatin, rosuvastatin, atorvasatin and/or simvastatin may be administered at 40 mg/d (Jacobson T A, et al: *Toward "Pain-Free" Statin Prescribing:Clinical Algorithm for Diagnosis and Management of Myalgia. Mayo Clin Proc. June* 2008; 83(6):687-700). This treatment may or may not also comprise the administration of a fibrate or ezetimibe (10 mg/d, Jacobson T A, et al: *Toward "Pain-Free" Statin Prescribing: Clinical Algorithm for Diagnosis and Management of Myalgia. Mayo Clin Proc. June* 2008; 83(6):687-700). Colesevelam may be additionally administered with ezetimibe at a dosage of 3.75 g/d (Joy T R and Hegele R A, *Narrative review: statin-related myopathy. Ann Intern Med.* 2009 Jun. 16; 150(12):858-68).

For the purposes of the present invention, a lipid lowering drug or medication is preferably an HMG-CoA reductase inhibitor, niacin (nicotinic acid), a cholesterol absorption inhibitor, a cholesteryl ester transfer protein (CETP) inhibitor, a bile acid sequestrant; a fibrate or a phytosterol. For the purposes of the present invention, a cholesterol absorption inhibitor is preferably ezetimibe or SCH-48461; a cholesteryl ester transfer protein (CETP) inhibitor is preferably torcetrapib, anacetrapib or dalcetrapib; a bile acid sequestrant is preferably colesevelam, cholestyramine or colestipol; and a librate is preferably fenofibrate, gemfibrozil, clofibrate, or bezafibrate.

As used herein, a subject includes all mammals, including without limitation humans, but also non-human primates, dogs, cats, horses, sheep, goats, cows, rabbits, pigs and rodents. A particularly preferred subject in accordance with the present invention is a human.

As used herein a high risk subject is typically a subject, particularly a human, on high statin dose and/or on multiple medications (causing a risk for drug interactions), having a known muscle disease, or having a disease that may increase the risk of adverse events (e.g., hypothyroidism, renal insufficiency or a liver disease).

As used herein, a control may be a control sample or merely a control value. In case it is a control value, it will be appreciated that it may have already been determined, calculated or extrapolated prior to initiating the methods of the invention. Alternatively, the control value may be determined, calculated or extrapolated after conducting the determination of the concentration(s) of said one or more lipid(s), or lipid-lipid concentration ratio(s), in accordance with the methods of the present invention. Thus, it will be appreciated that a suitable control value in accordance with the present invention may well be one that is taken from the literature.

A sample as used herein is defined as any biological sample obtained from a subject or a group or population of subjects. For the purposes of the present invention, the biological sample may be whole blood, blood serum, or blood plasma, with blood serum and blood plasma being preferred. The sample may also be urine. Taking a blood and/or urine sample of a patient is a part of normal clinical practice. The blood sample can be taken in connection with e.g. measuring the cholesterol levels in the patients. The collected blood sample can be prepared and serum or plasma can be separated with techniques well known to a person skilled in the art. Venous blood samples can be collected from patients using a needle and a BD Vacutainer® Plastic Tubes or Vacutainer® Plus Plastic Tubes (BD Vacutainer® SST™ Tubes contain spray-coated silia and a polymer gel for serum separation). Serum can be separated by centrifugation at 1300 RCF for 10 min at room temperature and stored in small plastic tubes at −80° C. The urine sample can be collected and prepared with techniques well know to a person skilled in art. The sample may also be a fraction of whole blood, blood plasma or blood serum, e.g., a lipoprotein fraction. In another preferred embodiment, the sample may also be a tissue sample, e.g., muscle biopsy tissue.

The lipids or other molecules in the control to which the comparison is made in accordance with the present invention are referred to herein also as control markers.

As used herein, the reference to a control sample from the same subject or from another) subject may mean that the control sample has been directly obtained from said subject. Alternatively, however, it may also mean that it has been obtained as the result of a physical or chemical treatment of a sample directly obtained or taken from said subject, such as centrifugation, fractionation, enzymatic digestion, precipitation, and the like. The same applies to any reference herein to a control sample from a group of subjects or from a population of subjects.

The terms control sample from a group of subjects or control sample from a population of subjects as used herein furthermore preferably entail that the control sample is representative of said group or population. In this context, representative shall mean that the concentration(s) of the one or more lipids or the lipid-lipid concentration(s) in said control sample to which a comparison is made in the context of the present invention corresponds to the average concentration(s) of said lipid(s) or lipid-lipid concentration ratio(s) in corresponding individual samples from the subjects of said group or population. Preferably, the concentrations of all lipids and lipid-lipid concentration ratios in said control sample correspond to the average concentrations of said lipids and lipid-lipid concentration ratios in corresponding individual samples from the subjects of said group or population. Likewise, where a comparison is made in the context of the present invention to one or more other molecules, e.g., other lipids or proteins, such as total PC, or apoA, apoB, or albumin, respectively, a representative control sample is one where the concentration(s) of this (these) molecule(s) correspond(s) to the average concentration(s) of said molecule(s) in corresponding individual samples from the subjects of said group or population. In a preferred embodiment, a control sample from a group of subjects or a control sample from a population of subjects in the sense of the present invention is obtained by mixing equal amounts of samples directly obtained or taken from the subjects of said group or population, or by mixing equal amounts of fractions, constituents or reaction products (e.g., enzymatic reaction products or precipitates) thereof.

As used herein a control sample corresponds to the subject's sample if it has been obtained from the same type of biological tissue or source in the same, or essentially the same, manner. For example, if the subject's sample is a whole blood, blood plasma, blood serum sample or urine, or a fraction thereof, a corresponding control sample will likewise be a whole blood, blood plasma, blood serum sample, or urine, or a fraction thereof, respectively. It will be appreciated that such corresponding control sample would include whole blood, blood plasma, blood serum samples, or urine, or a fraction thereof, obtained by mixing the whole blood, blood plasma, blood serum, or urine samples, or certain fractions thereof, from a group or population of subjects (see also the further explanations herein and the claims regarding suitable control samples in accordance with the invention). The same applies mutatis mutandis to, e.g., tissue samples.

A lipid as used herein is defined as hydrophobic or amphiphilic small molecule.

For the purposes of the present invention, lipids are referred to according to the following nomenclature: CE is cholesteryl ester, Cer is ceramide, DAG is diacylglycerol, PC O is ether-linked PC, Gb is Globotriaosylceramide, GD is disialogangliosides, Glc/GalCer is galactosyl- or glucosylceramides, GM is monosialogangliosides, LacCer is lactosylceramides, LPC is lysophosphatidylcholine, PC is phosphatidylcholine, PE is phosphatidylethanolamine, PI is phosphatidylinositol, SM is sphingomyelin, S1P is sphingosine-1-phosphate, HETE is hydroxyeicosatetraenoic acid, HEPE is hydroxyeicosapentaenoic acid, DHET is dihydroxyeicosatrienoic acid, PGE is prostaglandin E and AA is arachidonic acid.

The nomenclature X:Y indicates, X number of total carbon atoms in the fatty acid(s) portions of the molecule, and Y the total number of double bonds in the fatty acid portion(s) of the molecule.

The nomenclature A/B indicates, for a molecule of DAG and PC, A and B types of fatty acid moieties attached to the glycerol backbone of the molecule.

The nomenclature (dC/A) indicates, for a molecule of Cer, Gb, GlcCer, LacCer and SM, C the type of long-chain base with an amide-linked, A, fatty acid moiety.

15-HETE is formally known as (±)15-hydroxy-5Z,8Z, 11Z,13E-eicosatetraenoic acid (CAS: 73836-87-0) and is referred to in Lehmann, W. D., Metzger, K., Stephan, M., et al. *Quantitative lipoxygenase product profiling by gas chromatography negative-ion chemical ionization mass spectrometry*. Anal Biochem 224 227-234 (1995) and Zijlstra, F. J., van Dijk, A. P. M., Wilson, J. H. P., et al. 15-*HETE is the main eicosanoid formed by human colonic mucosa. Agents Actions* C53-059 (1992). 12-HETE is formally known as (±)12-hydroxy-5Z,8Z,10E,14Z-eicosatetraenoic acid (CAS: 71030-37-0) and is referred to in Lehmann, W. D., Metzger, K., Stephan, M., et al. *Quantitative lipoxygenase product profiling by gas chromatography negative-ion chemical ionization mass spectrometry*. Anal Biochem 224 227-234 (1995). O'Flaherty, J. T., Thomas, M. J., Lees, C. J., et al. *Neutrophil-aggregating activity of monohydroxyeicosatetra-*

*enoic acids.* Am J Pathol 104 55-62 (1981). LacCer(d18:1/22:0) is formally known as N-(docosanoyl)-1-b-lactosyl-sphing-4-enine and belongs to the same family as LacCer (d18:1/24:0) (CAS number is 105087-85-2). Gb3 is formally known as ceramide trihexoside (CAS: 71965-57-6) and is referred in Groener J E, Poorthuis B J, Kuiper S, Helmond M T, Hollak C E, Aerts J M. *HPLC for simultaneous quantification of total ceramide, glucosylceramide, and ceramide trihexoside concentrations in plasma.* Clin Chem. 2007 April; 53(4):742-7 and Mills K., Johnson A., Winchester B. *Synthesis of novel internal standards for the quantitative determination of plasma ceramide trihexoside in Fabry disease by tandem mass spectrometry.* FEBS Lett. 2002 Mar. 27; 515 (1-3):171-6. 12-HEPE is formally known as (±)-12-hydroxy-5Z,8Z,10E,14Z,17Z-eicosapentaenoic acid (CAS: 81187-21-5) and is referred in Karanian, J. W., Kim, H. Y., and Salem, N. *Inhibitory effects of n-6 and n-3 hydroxy fatty acids on thromboxane (U46619)-induced smooth muscle contraction.* J Pharmacol Exp Ther 270 1105-1109 (1994) and Takenaga, M., Hirai, A., Terano, T., et al. *Comparison of the in vitro effect of eicosapentaenoic acid (EPA)-derived lipoxygenase metabolites on human platelet function with those of arachidonic acid.* Thromb Res 37 373-384 (1986).

An agent capable of binding to any one of the lipidomic markers of the invention may be a small molecule (i.e., a molecule having a molecular weight of less than 5 kDa, and more typically less than 1 kDa, which may be a protein or a peptide sequence, or a member of any of a wide variety of organics, e.g., a carbohydrate, a sugar, a drug, an alcohol, a carboxylic acid, an amine, an aldehyde or a ketone, a thiol, a cyclic or an acyclic compound), a nucleic acid (e.g., an aptamer), a carbohydrate, a protein or peptide, or a proteoglycan. In a preferred embodiment, the agent is an antibody.

As used herein, the term antibody includes monoclonal and polyclonal antibodies, whole antibodies, antibody fragments, and antibody sub-fragments that exhibit specific binding to a said lipid. Thus, suitable antibodies can be whole immunoglobulins of any class, e.g., IgG, IgM, IgA, IgD, IgE, chimeric antibodies or hybrid antibodies with dual or multiple antigen or epitope specificities, or fragments, e.g., F(ab')$_2$, Fab', Fab and the like, including hybrid fragments, and additionally includes any immunoglobulin or any natural, synthetic or genetically engineered protein that acts like an antibody by binding to a specific antigen to form a complex. The term antibody encompasses antigen-binding fragments of antibodies (e.g., single chain antibodies, Fab fragments, F(ab')$_2$, a Fd fragment, a Fv fragment and dAb fragments) as well as complete antibodies. For example, Fab molecules can be expressed and assembled in a genetically transformed host like *E. coli.* A lambda vector system is available thus to express a population of Fab's with a potential diversity equal to or exceeding that of subject generating the predecessor antibody. See Huse W D, et al., *Science* 1989, 246:1275-81. Such Fab's are included in the definition of antibody. The ability of a given molecule, including an antibody fragment or sub-fragment, to act like an antibody and specifically bind to a specific antigen can be determined by binding assays known in the art, for example, using the antigen of interest as the binding partner.

Antibodies against lipids in accordance with the present invention may be prepared by methods well known to those skilled in the art. For example, mice may be immunized with a lipid with adjuvant. Splenocytes are harvested as a pool from the mice that were administered 3 immunizations at 2-week intervals with test bleeds performed on alternate weeks for serum antibody titers. Splenocytes are prepared as 3 aliquots that are either used immediately in fusion experiments or stored in liquid nitrogen for use in future fusions.

Fusion experiments are then performed according to the procedure of Stewart & Fuller, *J. Immunol. Methods* 1989, 123:45-53. Supernatants from wells with growing hybrids are screened by enzyme-linked immunosorbent assay (ELISA) for monoclonal antibody (MAb) secretors on 96-well ELISA plates coated with the said lipid. ELISA positive cultures are cloned by limiting dilutions, typically resulting in hybridomas established from single colonies after 2 serial cloning experiments.

EXAMPLES

Example 1

Materials and Methods

For this study the subjects were selected from a cohort of patients presenting clear muscular intolerance phenotypes determined according to strict criteria.

The inclusion criteria for the subjects were the following:
Written informed consent to participate in the study;
Men or women aged 18 years or older;
Documentation of statin-related muscle toxicity manifested by either:
  muscle pain that occurs during statin treatment and stops after withdrawal or reduction in dosage; or
  muscle pain that starts after initiation of statin treatment and persists while still being treated in patients in whom it is considered not possible to stop statin administration; or
  muscle pain that occurs while patient is being treated with a statin and clearly appears to be statin-related in the opinion of his/her physician; or
  patient in whom lipid-lowering regimen is changed from a statin to ezetimibe because of intolerance to statins due to muscle pain or weakness, myopathy or rhabdomyolysis; or
  elevation in plasma CK level more than 1.5 times the upper limit of normal while being treated with a statin, in the absence of other causes to explain the abnormality; or
  presence of myoglobinuria or myoglobinemia while being treated with a statin, in the absence of other causes to explain the abnormality;
  clinical diagnosis of rhabdomyolysis while being treated with a statin, in the absence of other responsible causes.

Exclusion Criteria for the subjects were the following:
patient in whom muscle pain is not clearly associated with the use of a statin in the physician's judgment;
Hypothyroidism that is not controlled with a stable dose of supplement for at least the last 3 months and that occurred during muscle toxicity;
Known hyperthyroidism in the last year and that occurred during muscle toxicity;
History of alcohol or drug abuse in the last year and that occurred during muscle toxicity;
Known renal insufficiency (not secondary to rhabdomyolysis) with serum creatinine level of 200 μmol/L or more at the time of muscle toxicity;
Known severe liver disease with cirrhosis, biliary obstruction, acute or chronic infectious hepatitis at the time of the muscle toxicity;
Known hereditary or acquired muscle disease;

Any medical or psychiatric condition that may make the patient an unsuitable candidate for the study in the physician's opinion.

Participation in any other investigational drug study within 30 days of recruitment.

Inclusion Criteria for the controls were the following:
Written informed consent to participate in the study
Men or women aged 18 years or older;
Known dyslipidemia treated with a stable dose of a statin for at least 3 months;
Absence of current or past statin-related side effects.

Exclusion Criteria for the controls were the following:
Hypothyroidism that is not controlled with a stable dose of supplement for at least the last 3 months unless the absence of muscle toxicity due to statins has been confirmed before condition;
Known hyperthyroidism in the last year unless the absence of muscle toxicity due to statins has been confirmed before condition;
History of alcohol or drug abuse in the last year unless the absence of muscle toxicity due to statins has been confirmed before condition;
Known renal insufficiency with serum creatinine level of 200 µmol/L or more at the time of recruitment unless the absence of muscle toxicity due to statins has been confirmed before condition;
Known severe liver disease with cirrhosis, biliary obstruction, acute or chronic infectious hepatitis at the time of recruitment unless the absence of muscle toxicity due to statins has been confirmed before condition;
Known hereditary or acquired muscle disease;
Any medical or psychiatric condition that may make the patient an unsuitable candidate for the study in the physician's opinion.
Participation in any other investigational drug study within 30 days of recruitment.

TABLE 2

Background characteristics for statin myopathy patients analyzed with Lipidomics

|  | N= | Atorvastatin equivalent dose | Age | CK |
|---|---|---|---|---|
| Controls male | 92 | 35 | 63.5 | 96.3 |
| Controls female | 58 | 28 | 64.3 | 87.8 |
| Cases male, CK < 200 U/l | 50 | 28 | 64.1 | 98.5 |
| Cases male, CK > 200 U/l | 42 | 37 | 60 | 271 |
| Cases female, CK < 200 U/l | 50 | 25 | 62 | 76 |
| Cases female, CK > 200 U/l | 8 | 26 | 64 | 267 |
| Total number of subjects | 300 |  |  |  |

Analytical Methods

Mass Spectrometry Driven Lipidomics

Direct infusion coupled to tandem mass spectrometry, i.e. shotgun lipidomics, and two liquid chromatography tandem mass spectrometry (LC-MS/MS) approaches, i.e. ceramide and cerebroside lipidomics and eicosanoid lipidomics, were used to identify statin-induced muscle toxicity by analyzing molecular lipid species in human plasma. The applied methods were optimized especially for quantification of molecular cholesteryl esters (CE), phosphatidylcholines (PC), lysophosphatidylcholines (LPC) and other lysophospholipids (LPL), ether-linked phosphatidylcholines (PC O) and other ether-linked phospholipids (PL O), phosphatidylserines (PS), phosphatidylethanolamines (PE), phosphatidylglycerols (PG), phosphatidylinositols (PI), phosphatidic acids (PA), diacylglycerols (DAG), ceramides (Cer), glucosylceramides (GlcCer), lactosylceramides (LacCer), globotriaosylceramides (Gb), free fatty acids (FFA) and eicosanoids.

The following materials were used according to the methods. HPLC or LC-MS grade of chloroform, methanol, water, acetonitrile, formic acid, methanol, isopropanol, ammonium acetate, acetic acid, potassium chloride and butylated hydroxytoluene (BHT) were purchased from Sigma-Aldrich (St. Louis, Mo., USA).

HPLC column (Acquity BEH C18, 2.1×50 mm id. 1.7 µm) was purchased from Waters (Milford, Mass., USA). HPLC pre-column (Widepore C18 4×2.0 mm) was purchased from Phenomenex (Torrance, Calif., USA). All labware used for the extraction were resistant to chloroform. Aerosol resistant filter tips (Molecular BioProducts) and Eppendorf 2 ml safe-lock tubes, 96-well twin.tec PCR plates, and Pierce-it-lite thermo-sealing foils were purchased from VWR International (West Chester, Pa., USA). CO-RE Filter Tips and 96-well 2 ml Whatman Uniplates were purchased from Hamilton Robotics (Bonaduz, Switzerland). Synthetic lipid standards were purchased from Avanti Polar Lipids (Alabaster, Ala., USA), Matreya (Pleasant Gap, Pa., USA), and Cayman Chemical (Ann Arbor, Mich., USA).

Lipids were extracted in chloroform:methanol according to the following protocols. Samples were spiked with known amounts of non-endogenous synthetic internal standards for data normalization and endogenous lipid quantification. Post-extract spiked non-endogenous synthetic external standards were used for quality controlling. Stock solutions of standards were prepared by dissolving appropriately weighed amounts of each standard in chloroform:methanol (2:1, v/v) to achieve a final concentration of 500 µM. An internal standard mixture containing each of the standard stock was created and used in lipid extraction.

5 µl of plasma was used for shotgun lipidomics and 10 µl of plasma for ceramide and cerebroside lipidomics Lipid extractions were carried out in automated fashion using a Hamilton MICROLAB STAR system (Hamilton Robotics, Switzerland). Well-mixed samples were aliquoted into a 96-well 2 ml Whatman Uniplate containing ice-cold methanol and 0.1% BHT. The samples were mixed thoroughly after each step in the extraction protocol. The extraction proceeded at room temperature by adding an appropriate volume of internal standard mixture and chloroform and methanol. In shotgun and ceramide and cerebroside lipidomics, the organic phase separation was facilitated by adding 20 mM acetic acid and centrifuging the plate for 5 min at 500×g. The organic phase was transferred into a new 96-well 2 ml Whatman Uniplate. The remaining water-containing phase was washed by adding appropriate volume of chloroform followed by centrifugation. The two organic phases were pooled and evaporated under $N_2$ until dryness. The lipid extracts were then re-dissolved in chloroform:methanol (1:2, v/v) including the addition of the synthetic external standard. The extracts were stored in 2 ml safe-lock Eppendorf tubes at –20° C. prior to MS analysis. Required volumes of lipid extracts were aliquoted into an Eppendorf 96-well twin.tec PCR plate and the plate was heat-sealed with aluminum foil to avoid evaporation.

In shotgun lipidomics, lipid extracts were analyzed on a hybrid triple quadrupole/linear ion trap mass spectrometer (QTRAP 5500, AB Sciex) equipped with a robotic nanoflow ion source (NanoMate HD, Advion Biosciences). The instruments were operated in positive and negative ion modes. In positive ion the spray voltage was set to 1.0 to 1.4 kV and in negative ion mode to –1.0 to –1.4 kV. A gas pressure of 0.3-0.8 psi was used and the interface heater was set at 60° C. The collision energy (CE) and declustering potential (DP) was optimized for each lipid class using synthetic standards. The mass spectrometer was operated in unit resolution mode using a scan speed of 200 Da/s. Molecular lipids were analyzed in both positive and negative ion modes using multiple precursor ion scanning (MPIS) and neutral loss scanning (NLS) as described by Stahlman and colleagues (Stahlman M, et al: *High-throughput shotgun lipidomics by quadrupole time-of-flight mass spectrometry. J Chromatogr B Analyt Technol Biomed Life Sci* 2009).

In ceramide and cerebroside lipidomics, the high performance liquid chromatography (HPLC) analyses were conducted in the following way. Chromatographic apparatus consisted of a CTC HTC PAL autosampler (CTC Analytics AG, Switzerland), a Rheos Allegro UHPLC pump (Flux Instruments AG, Switzerland), an external column heater set to 60° C. for ceramide and cerebroside lipidomics and the Acquity BEH C18 column with an in-line pre-column. The extracted samples, 10 µl of each, were injected into the pre-column followed by the analytical column and delivered to the mass spectrometer at a flow rate of 500 µl/min. In ceramide and cerebroside lipidomics, A gradient was used for lipid analyte separation with solvent A comprising 10 mM ammonium acetate in HPLC grade water containing 0.1% formic acid and solvent B of 10 mM ammonium acetate in acetonitrile:isopropanol (4:3, v/v) containing 0.1% formic acid. The gradient was constructed in the following way: 0 min-65% B; 2 min-65% B; 2.5 min-75% B; 17.5 min-100% B; 22.5 min-100% B; 22.6 min-65% B; 25 min-65% B.

The lipid extracts were analyzed by HPLC-MS/MS. The MS analysis was performed on a hybrid triple quadrupole/linear ion trap mass spectrometer equipped with the Turbo V™ Ion Source (4000 QTRAP, AB Sciex). The instrument was operating in positive ion mode. The ion source voltage was set to 5500V for ceramide and cerebroside lipidomics and to −4500V for ganglioside lipidomics, and source temperature at 400° C. The collision energy (CE) and declustering potential (DP) was optimized for each lipid class using synthetic standards. A 20 sec dwell time was applied for each scan. Multiple reaction monitoring (MRM) scan mode was applied and based on the description by Sullards and colleagues (Sullards M C, et al: *Structure-specific, quantitative methods for analysis of sphingolipids by liquid chromatography-tandem mass spectrometry: "inside-out" sphingolipidomics. Methods Enzymol* 2007).

Eicosanoids were extracted using solid phase extraction (SPE). 150 µl plasma was extracted with 10% methanol containing 0.1% of butylated hydroxytoluene (BHT). Samples were spiked with known amounts of non-endogenous synthetic internal standards for data normalization and endogenous lipid quantification. An internal standard mixture containing each of the standard stock was created and used in lipid extraction. Strata-X 33 um SPE cartridges were conditioned with HPLC grade methanol followed by a conditioning step with ultra pure water (UPW). Samples were loaded onto the SPE followed by a wash step using 35% methanol. Eicosanoids were eluted with acetonitrile and the sample elutes were dried down under nitrogen. The final sample extracts were reconstituted in methanol and directly analyzed by mass spectrometry.

In the analysis for Eicosanoids, high performance liquid chromatography (HPLC) analyses were conducted in the following way: Chromatographic apparatus consisted of a CTC HTC PAL autosampler (CTC Analytics AG, Switzerland), a Rheos Allegro UHPLC pump (Flux Instruments AG, Switzerland), an external column heater set to 45° C. and switching valve (Valco Instruments Co. Inc. and VICI AG, Huston, USA). Separation was carried out using a Phenomenex Jupiter, 250×2.0 mm id. 5 µm HPLC column (Phenomenex, Inc, Torrance, Calif.). The extracted samples, 10 µl of each, were injected into the analytical column and delivered to the mass spectrometer at a flow rate of 300 µl/min. A gradient was used for lipid analyte separation with solvent A comprising of acetonitrile:water (63:37 (v/v)) containing 0.1% formic acid and solvent B of acetonitrile:isopropanol (50:50 (v/v)). The gradient was constructed in the following way: 0 min-0% B; 6 min-20% B; 6.50 min-55% B; 10.0 min-55% B; 12.0 min-100% B; 14.0 min-100% B; 14.50 min-0% B; 18.0 min-0% B.

The lipid extracts were analyzed by HPLC-MS/MS. The MS analysis was performed on a hybrid triple quadrupole/linear ion trap mass spectrometer equipped with the Turbo V™ Ion Source (4000 QTRAP, AB Sciex). The instrument was operating in negative ion mode and the ion source voltage was set to −4500V. The collision energy (CE) and declustering potential (DP) was optimized for each lipid class using synthetic standards where available. Multiple reaction monitoring (MRM) scan mode was applied and based on the description by Deems and colleagues (Deems, R., et al: *Detection and quantitation of eicosanoids via high performance liquid chromatography-electrospray ionization-mass spectrometry. Methods Enzymol* 2007).

The data processing was done in the following way: Initially the retention time (in LC mode) and identification of each peak was done using endogenous standards and by Information Dependent Acquisition (IDA) experiments where applicable. The raw data were processed according to peak detected and retention time (in LC mode) in automated fashion. A stringent cutoff was applied for separating background noise from actual lipid peaks. Each sample was controlled and only accepted when fulfilling the stringent acceptance criteria. Peak area counts (cps) of detected peaks were converted into a list of corresponding lipid names. Lipids were normalized to their respective internal standard and sample volume to retrieve their concentrations.

The ratio of synthetic Internal Standards (IS) to corresponding post-extract spiked External Standards (ES), and MS analysis of extracted matrix and solvents served as quality controls (QC) of the analysis. In addition, extracted reference plasma samples were analyzed for monitoring the instruments' performance, i.e., the intra- and inter-assay variation.

A calibration line using synthetic or isolated standards was obtained prior to sample analysis. Synthetic standards were chosen based on application and had similar properties to the endogenous lipids or analyte(s) of interest. The calibration line consisted of a minimum of five standards points covering the expected quantification range. The calibration line was used to determine the dynamic quantification range for each lipid class monitored, e.g., the linear quantification limits. As the internal standards used behave in the same way as endogenous lipids they were used for quantifying endogenous lipid species. The calibration lines were based on the same internal standards that were used for quantification of the endogenous lipids.

For each platform, a stringent cutoff was applied for separating background noise from actual lipid peaks. Each sample was controlled and only accepted when fulfilling the acceptance criteria. Masses and counts of detected peaks were converted into a list of corresponding lipid names. Lipids were normalized to their respective internal standard and sample volume to retrieve their concentrations.

Statistical Analyses

Percentage changes in lipid concentrations between control and case groups were calculated as follows:

100*(AVG[C] in case group−AVG[C] in control group)/AVG[C] in control group.

Statistical significance was assigned based on two independent samples t-test and Mann-Whitney U-test p-values.

In addition, ROC curves were used for finding lipid molecules and concentration cutoffs that separate the best cases from controls. Sensitivity is calculated as a number of correctly identified cases divided by the total number of cases. Specificity is calculated as a number of correctly identified controls divided by the total number of controls. Sensitivity and specificity was calculated for each lipid concentration. Significant biomarkers were defined as those molecules that have a t-test based p-value of 0.05 or Sensitivity>=60% and Specificity=>40%. Gender groups were also analyzed separately in order to avoid any unexpected gender specific results as men are generally more muscular and physically active.

Results

In the study sample group the creatine kinase levels were practically identical in controls and cases, therefore this traditionally used enzyme marker was not predictive or diagnostic for statin-induced myopathy.

On the other hand, lipidomic biomarkers appeared as significant biomarkers of the statin-induced myopathy. A total of 290 molecular lipids were quantified in this study as described above. Out of those 20 molecular lipids were significant biomarkers based on set statistical criteria. The significant biomarker candidates based on molecular lipid concentrations are presented in Table 3.

The preferred embodiments selected among the identified biomarker candidates are listed in Table 5.

TABLE 3

Significant biomarkers based on individual lipid or fatty acid measurement. Species names, p-values, percentage change, auc-values; and specificity and sensitivity are presented.

| Measurement Name | Percentage Change | p-value | AUC | Sensitivity | Specificity |
|---|---|---|---|---|---|
| Increased | | | | | |
| 12-HETE | 460.03 | 0.0001 | 0.77 | 71.43 | 62.79 |
| LacCer(d18:1/22:0) | 65.01 | 0.0002 | 0.72 | 69.39 | 60.42 |
| 15-HETE | 49.64 | 0.0150 | 0.63 | 63.64 | 60.61 |
| Gb3(d18:1/24:1) | 43.93 | 4.18 × 10$^{-6}$ | 0.78 | 85.71 | 61.90 |
| Gb3(d18:1/22:0) | 43.21 | 0.0378 | 0.78 | 87.50 | 62.50 |

TABLE 3-continued

Significant biomarkers based on individual lipid or fatty acid measurement. Species names, p-values, percentage change, auc-values; and specificity and sensitivity are presented.

| Measurement Name | Percentage Change | p-value | AUC | Sensitivity | Specificity |
|---|---|---|---|---|---|
| Gb3(d18:1/24:0) | 40.21 | 0.0295 | 0.80 | 87.50 | 62.50 |
| LacCer(d18:1/24:0) | 31.81 | 0.0110 | 0.61 | | |
| AA | 30.59 | 0.0005 | 0.72 | 77.55 | 60.00 |
| Total eicosanoids | 24.18 | 0.0023 | 0.70 | 73.47 | 60.00 |
| Total Gb3 | 23.40 | 0.0006 | 0.69 | 64.29 | 71.43 |
| Cer(d18:1/20:0) | 20.96 | 0.0145 | 0.62 | | |
| Gb3(d18:1/20:0) | 20.22 | 0.0219 | 0.65 | 66.67 | 61.29 |
| LacCer(d18:1/24:1) | 14.52 | 0.0213 | 0.62 | | |
| Decreased | | | | | |
| Gb3(d18:1/16:0) | −7.73 | 0.0220 | 0.61 | | |
| Total LacCer* | −10.10 | 0.0347 | 0.64 | 64.00 | 68.00 |
| LacCer(d18:1/16:0)* | −11.70 | 0.0168 | 0.66 | 66.00 | 60.00 |
| Gb3(d18:1/18:0) | −14.34 | 0.0145 | 0.65 | 67.35 | 60.42 |
| 14_15-DHET | −16.24 | 0.0468 | 0.60 | | |
| Glc/GalCer(d18:1/24:1)* | −17.09 | 0.0050 | 0.66 | 70.00 | 68.00 |
| 8_9-DHET | −22.67 | 0.0394 | 0.64 | 60.00 | 68.18 |

*The markers are specific for females. Other markers are not gender specific.

Lipid measurements that were below a detection limit in at least 25% of control or case samples were converted into dichotomous variables where 0 indicates that a lipid is absent and 1 indicated that a lipid is present in a sample. Next, we counted how many times a given lipid was present in controls and cases and significance of the fact that lipids were missing/present in controls comparing to cases was evaluated using Fisher exact test. Table 4 shows the potential biomarkers generated with Fisher test.

TABLE 4

Significant markers generated by Fisher test

| LIPID_NAME | Control absent | Control present | Case absent | Case present | Fisher p-value | Direction of change |
|---|---|---|---|---|---|---|
| LacCer (d18:1/20:0) | 32 | 18 | 20 | 30 | 0.02718 | Increased |
| 12-HEPE | 36 | 14 | 13 | 37 | 7.70E−06 | Increased |
| PGE2 | 47 | 3 | 37 | 13 | 0.01222 | Increased |
| 12-OXOETE | 28 | 12 | 12 | 28 | 0.000695 | Increased |
| 17-HDoHE | 31 | 9 | 19 | 21 | 0.010492 | Increased |
| PGD2 | 39 | 1 | 29 | 11 | 0.003255 | Increased |
| TXB3 | 38 | 2 | 19 | 21 | 0.000003 | Increased |
| PS 18:0/18:1 | 34 | 6 | 25 | 15 | 0.040609 | Increased |
| SM (d18:1/24:2) | 30 | 10 | 20 | 20 | 0.036835 | Increased |

TABLE 5

Preferred embodiments of biomarkers

| Measurement Name | Percentage Change | p-value | AUC | Sensitivity | Specificity |
|---|---|---|---|---|---|
| Increased | | | | | |
| 12-HETE | 460.03 | 0.0001 | 0.77 | 71.43 | 62.79 |
| LacCer(d18:1/22:0) | 65.01 | 0.0002 | 0.72 | 69.39 | 60.42 |
| Gb3(d18:1/24:1) | 43.93 | 0.0000 | 0.78 | 85.71 | 61.90 |
| Decreased | | | | | |
| LacCer(d18:1/16:0)* | −11.70 | 0.0168 | 0.66 | 66.00 | 60.00 |
| Glc/GalCer(d18:1/24:1)* | −17.09 | 0.0050 | 0.66 | 70.00 | 68.00 |

*The markers are specific for females. Other markers are not gender specific.

Furthermore, the significance of lipid-lipid concentration ratios for identifying the statin-induced myopathy was investigated. The lipid-lipid concentration ratios which showed improved AUC values over individual lipids are shown in Table 6. Table 6 shows that, in addition to the individual lipid measurements, the lipid-lipid concentration ratios can be used as biomarkers to identify the statin-induced myopathy or for determining whether the statin treatment or the treatment with a lipid lowering drug of a subject needs adjustment.

TABLE 6

Example on the lipid-lipid concentration ratios and their significance

| Measurement name | AUC | Sensitivity | Specificity | p-value | Percentage change |
|---|---|---|---|---|---|
| Increased | | | | | |
| 12-HETE/15-HETrE | 0.83 | 83.3 | 61.9 | 0.0000195733 | 635.0 |
| 12-HETE/14_15-DHET | 0.79 | 73.5 | 62.8 | 0.0000278151 | 587.8 |
| 12-HETE/Gb3(d18:1/16:0) | 0.80 | 70.8 | 71.4 | 0.0002342687 | 494.8 |
| 12-HETE/Glc/GalCer(d18:1/24:1) | 0.78 | 70.8 | 71.4 | 0.0003976485 | 484.5 |
| 12-HETE/Glc/GalCer(d18:1/18:0) | 0.78 | 70.8 | 76.2 | 0.0002044722 | 477.8 |
| Gb3(d18:1/24:1)/LacCer(d18:1/16:0) | 0.82 | 83.3 | 61.9 | 0.0000042133 | 54.4 |
| LacCer(d18:1/22:0)/LacCer(d18:1/24:1) | 0.71 | 74.0 | 60.0 | 0.0004157530 | 26.1 |
| Cer(d18:1/20:0)/Glc/GalCer(d18:1/24:1) | 0.72 | 74.0 | 62.0 | 0.0006147547 | 25.8 |
| Decreased | | | | | |
| LacCer(d18:1/16:0)/LacCer(d18:1/22:0) | 0.69 | 74.0 | 66.0 | 0.0009722258 | −20.9 |
| Gb3(d18:1/16:0)/Gb3(d18:1/24:1) | 0.80 | 83.3 | 61.9 | 0.0000005500 | −23.9 |
| 11-HETE/12-HETE | 0.85 | 87.8 | 65.1 | 0.0000000008 | −59.1 |

In summary, this study provides novel lipid markers of statin-induced muscle toxicity. Since the creatine kinase levels in the study sample group were practically identical in controls and cases (Table 2), the lipidomic biomarkers were more specific and sensitive markers of the statin-induced muscle toxicity.

The invention claimed is:

1. A method for determining whether a subject undergoing treatment with a lipid lowering drug is at risk to develop, or is suffering from muscle toxicity induced by the lipid lowering drug and/or one or more of its complications, wherein the one or more complications are selected from myalgia, myositis, myopathy, and rhabdomyolysis, the method comprising:
  (a) determining in a sample from said subject undergoing treatment with the lipid lowering drug the concentration(s) of one or more lipid(s), wherein the sample is whole blood, blood plasma, blood serum, muscle biopsy tissue, or urine, and wherein the one or more lipid(s) is (are) an eicosanoid selected from: 12-hydroxyeicosatetraenoic acid (HETE), 15-HETE, arachidonic acid (AA), 12-HEPE (hydroxyeicosapentaenoic acid), 14_15-DHET (dihydroxyeicosatrienoic acid) and $8_{13}$ 9-DHET;
  (b) comparing the concentration of the one or more lipid(s) to a control; and
  (c) determining whether the subject is at risk to develop, or is suffering from muscle toxicity induced by the lipid lowering drug and/or one or more of its complications, wherein (an) increased concentration(s) of one or more of 12-HETE, 15-HETE, AA, or 12-HEPE in said sample or decreased concentration(s) of one or more of $14_{13}$ 15-DHET or $8_{13}$9-DHET in said sample, when compared to the control, is (are) indicative of said subject suffering from said muscle toxicity induced by the lipid lowering drug and/or said complication(s), wherein the lipid concentration(s) is (are) determined by using mass spectrometry, and wherein if the concentration of the one or more of 12-HETE, 15-HETE, AA, or 12-HEPE is increased or the concentration of the one or more of 14_15-DHET or 8_9-DHET is decreased, as compared to the control, the method further comprises after step (c), a step of:
  i) reducing a statin dose;
  ii) stopping a statin treatment
  iii) changing to a different statin drug; or
  iv) changing to a different lipid lowering drug.

2. The method of claim 1, wherein the muscle toxicity is associated with a muscle disease.

3. The method of claim 2, wherein the muscle disease is a muscle dystrophy.

4. The method of claim 1, wherein the lipid lowering drug is a statin and the muscle toxicity is induced by the statin.

5. A method for determining whether the treatment with a lipid lowering drug of a subject undergoing treatment with a lipid lowering drug needs adjustment, comprising
  (a) determining in a sample from said subject undergoing treatment with the lipid lowering drug the concentration(s) of one or more lipid(s), wherein the sample is whole blood, blood plasma, blood serum, muscle biopsy tissue, or urine, and wherein the one or more lipid(s) is (are) an eicosanoid selected from: 12-hydroxyeicosatetraenoic acid (HETE), 15-HETE, arachidonic acid (AA), 12-HEPE (hydroxyeicosapentaenoic), acid $14_{13}15$-DHET (dihydroxyeicosatrienoic acid) and $8_{13}9$-DHET;
  (b) comparing the concentration of the one or more lipid(s) to a control; and
  (c) determining whether to adjust the treatment of the subject with the lipid lowering drug,
  wherein (an) increased concentration(s) of one or more of 12-HETE, 15-HETE, AA, or 12-HEPE in said sample or decreased concentration(s) of one or more of 14_15-DHET or $8_{-9}$-DHET in said sample, when compared to the control, is (are) indicative of said treatment requiring adjustment, wherein the lipid concentration(s) is (are) determined by using mass spectrometry, and
  wherein if the concentration of one or more of 12-HETE, 15-HETE, AA, or 12-HEPE is increased or the concentration of one or more of $14_{13}15$-DHET or $8_{13}9$-DHET is decreased as compared to the control, the method further comprises after step (c), a step of:
  i) reducing a statin dose;
  ii) stopping a statin treatment;

iii) re-commencing a statin treatment;
iv) changing to a different statin drug; or
v) changing to a different lipid lowering drug.

6. The method of claim 5, wherein the adjustment of said treatment with a lipid lowering drug further comprises a cessation of another drug treatment which led to muscle toxicity due to its interaction with one or more statins.

7. The method of claim 5, wherein the lipid lowering drug is a statin.

8. The method of claim 1 or 5, wherein the lipid whose increase in concentration is compared to the control is 12-HETE.

9. The method of claim 1 or 5, wherein the method is for evaluating the degree of muscle toxicity induced by a novel lipid lowering medication in a subject undergoing treatment with said lipid lowering medication.

10. The method of claim 1 or 5, comprising determining at least 2, at least 3, at least 4, or at least 5, of said lipid concentrations.

11. The method of claim 1 or 5, wherein said lipid lowering drug is a statin and wherein
 (a) said subject is being treated with one or more statins;
 (b) said subject had undergone statin treatment, but discontinued said treatment due to onset of muscle pain; or
 (c) said subject has not yet been treated with statins.

12. The method of claim 1 or 5, wherein the lipid lowering drug is a statin and the subject is at a high risk for developing statin-induced muscle toxicity and/or one or more of its complications.

13. The method of claim 1 or 5, wherein said lipid lowering drug is a statin and said control to which comparison is made is:
 (a) a control sample from the same subject undergoing statin treatment prior to the onset of muscle toxicity;
 (b) a control sample from the same subject prior to statin treatment or during discontinuation of statin treatment;
 (c) a control sample from a subject with no signs or history of statin-induced muscle toxicity;
 (d) a control sample from a population of subjects with no signs or history of statin-induced muscle toxicity;
 (e) a control value established from one or more subject(s) not on statin treatment and with no signs or history of muscle toxicity; or
 (f) a control value established from one or more subject(s) on statin treatment and with no signs or history of muscle toxicity.

14. The method of claim 1 or 5, further comprising determining or evaluating the level of creatine kinase in said subject or in a sample from said subject.

15. The method of claim 14, wherein the subject has or does not have elevated creatine kinase levels.

16. The method of claim 1 or 5, wherein
 said lipid lowering drug is a statin and wherein said statin is selected from the group consisting of atorvastatin, cerivastatin, fluvastatin, fluvastatin XL, lovastatin, pitavastatin, pravastatin, rosuvastatin simvastatin and combinations thereof.

17. The method of claim 1 or 5, further comprising a step of collecting the sample from the subject prior to step (a).

18. The method of claim 1 or 5, further comprising a step of extracting the eicosanoid from the sample to produce an eicosanoid extract.

19. The method of claim 1 or 5, wherein said lipid lowering drug is a 3-hydroxy-3-methyl-glutaryl (HMG)-CoA reductase inhibitor, niacin (nicotinic acid), a cholesterol absorption inhibitor, a cholesteryl ester transfer protein (CETP) inhibitor, a bile acid sequestrant, a fibrate, or a phytosterol.

20. The method of claim 19, wherein said cholesterol absorption inhibitor is ezetimibe or SCH-48461; said cholesteryl ester transfer protein (CETP) inhibitor is torcetrapib, anacetrapib or dalcetrapib; said bile acid sequestrant is colesevelam, cholestyramine or colestipol; and said fibrate is fenofibrate, gemfibrozil, clofibrate, or bezafibrate.

* * * * *

UNITED STATES PATENT AND TRADEMARK OFFICE
CERTIFICATE OF CORRECTION

PATENT NO. : 9,541,565 B2  
APPLICATION NO. : 13/332773  
DATED : January 10, 2017  
INVENTOR(S) : Reijo Laaksonen et al.

Page 1 of 1

It is certified that error appears in the above-identified patent and that said Letters Patent is hereby corrected as shown below:

In the Claims

Claim 1, Column 25, Line 53, "$8_{13}$ 9-DHET" should read --8_9-DHET--.

Claim 1, Column 25, Line 62, "$14_{13}$ 15-DHET or $8_{13}$9-DHET;" should read --14_15-DHET or 8_9-DHET;--.

Claim 1, Column 26, Line 7, "treatment" should read --treatment;--.

Claim 5, Column 26, Line 47, "$14_{13}$15-DHET" should read --14_15-DHET--.

Claim 5, Column 26, Line 48, "$8_{13}$9-DHET" should read --8_9-DHET--.

Claim 5, Column 26, Line 56, "8_$_9$-DHET" should read --8_9-DHET--.

Claim 5, Column 26, Line 63, "$14_{13}$15-DHET or $8_{13}$9-" should read --14_15-DHET or 8_9- --.

Signed and Sealed this  
Eighteenth Day of April, 2017

Michelle K. Lee  
*Director of the United States Patent and Trademark Office*